United States Patent [19]
Wickersheim

[11] Patent Number: 5,304,809
[45] Date of Patent: Apr. 19, 1994

[54] LUMINESCENT DECAY TIME MEASUREMENTS BY USE OF A CCD CAMERA

[75] Inventor: Kenneth A. Wickersheim, Menlo Park, Calif.

[73] Assignee: Luxtron Corporation, Santa Clara, Calif.

[21] Appl. No.: 945,229

[22] Filed: Sep. 15, 1992

[51] Int. Cl.$^5$ .................. G01K 11/00; G01N 21/64
[52] U.S. Cl. .................. 250/458.1; 250/459.1; 374/161
[58] Field of Search .................. 250/459.1, 458.1; 374/161

[56] References Cited

U.S. PATENT DOCUMENTS

| | | | |
|---|---|---|---|
| 2,551,650 | 5/1951 | Urbach | 250/337 |
| 2,642,538 | 6/1953 | Urbach | 250/316.1 |
| 3,639,765 | 2/1972 | Kleinerman | 250/330 |
| 4,061,578 | 12/1977 | Kleinerman | 250/330 |
| 4,215,275 | 7/1980 | Wickersheim | 374/137 |
| 4,455,741 | 6/1984 | Kolodner | 437/8 |
| 4,708,494 | 11/1987 | Kleinerman | 374/161 |
| 4,710,033 | 12/1987 | Hirano et al. | 374/161 |
| 4,789,992 | 12/1988 | Wickersheim et al. | 374/161 |
| 4,819,658 | 4/1989 | Kolodner | 128/736 |
| 4,877,965 | 10/1989 | Dandliker et al. | 250/458.1 |

OTHER PUBLICATIONS

Paul Kolodner and J. Anthony Tyson, "Microscopic fluorescent imaging of surface temperature profiles with 0.01°C resolution." *Appl. Phys. Lett.*, vol. 40, No. 9 (May 1, 1982) pp. 782–784.
Wood, *Physical Optics*. 3rd edition (Place and date of publication unknown) pp. 665–666.
Sholes, R. R. et al., "Fluorescent decay thermometer with biological applications", *Rev. Sci. Instrum. 51(7)*, pp. 882–884, (Jul. 1980).
Jensen, E. M. et al., "Optical Technique for Measurement of Currents Induced by Microwave Frequency Radiation: I. Basic Technology and Instrument Design", pp. T15.1–T15.6.
Urbach, F. et al., "The Observation of Temperature Distributions and of Thermal Radiation by Means of Non-Linear Phosphors", *Journal of the Optical Society of America*, vol. 39, No. 12, pp. 1011–1019, (Sep. 12, 1949).
Weber, M. J. et al., "Optical spectra and relaxation of $Cr^{3+}$ ions in $YAlO_3$", *Journal of Applied Physics*, vol. 45, No. 2, pp. 810–816, (Feb. 1974).
Masi, C. G. et al., "Finding Board Faults with Thermal Imaging", *Test & Measurement World*, pp. 109–121, (Mar. 1989).
Gartenberg, E. et al., "Twenty-Five Years of Aerodynamic Research with Infrared Imaging", *Journal of Aircraft*, vol. 29, No. 2, pp. 161–171, (Mar.–Apr. 1992).
Noel, B. W., et al., "Two-Dimensional Temperature Mapping Using Thermographic Phosphors", *Los Alamos National Laboratory*, pp. 1–15, presented at the 'High Temperature Sensors Symposium, 177th Meeting of the Electrochemical Society Montreal, Quebec, Canada, May 6–11, 1990, but unpublished.
Bugos, A. R. et al., "Remote Sensing with Thermophosphors", *Sensors*, pp. 17,19 and 20 (Mar. 1990).

*Primary Examiner*—Constantine Hannaher
*Attorney, Agent, or Firm*—Majestic, Parsons, Siebert & Hsue

[57] ABSTRACT

A video camera of a type using an array of charge coupled devices (CCDs) is utilized to measure a condition, such as temperature, by imaging onto the camera a luminescent signal which contains information of the signal's decay time. The luminescent decay time is measured by comparing, such as by ratioing, the integrated signal values obtained in successive frames of operation of the CCD. One application includes use to measure a two-dimensional temperature distribution across a surface. The surface of interest is either coated with a layer of the luminescent material or emissions from the surface are imaged onto a separate luminescent screen. Another application is as a multiplexer and detector system for a large array of optical fiber sensors, a luminescent signal from each of the sensors being imaged through its respective fiber onto a unique one or more of CCD photosites.

22 Claims, 5 Drawing Sheets

LUMINESCENT DECAY TIME MEASUREMENTS BY USE OF A CCD CAMERA

BACKGROUND OF THE INVENTION

This invention relates generally to techniques for measuring a decaying electromagnetic radiation signal, and, more specifically, to the measurement of a decay time of a luminescence signal that is generated in a material exposed to some parameter to be measured thereby. Measurement of temperature is extensively discussed herein but the invention is not limited to temperature applications.

One such application is the remote, real-time measurement of surface temperature distributions. In wind tunnel experiments with aircraft models, for example, a sequence of thermal images of the surface of the model aircraft may be acquired as part of the test data. Changes in the temperature distribution across the surface of an operating electronic component or complete circuit board is another application. In the medical field, medical thermography involves a thermal imaging of a skin area of a patient to provide information helpful to diagnosing the patient's condition. One way of doing this is to scan an infrared image of the surface across a point detector having an appropriate response to obtain electronic signals which are then used to display an image in visible light. The significant disadvantage of this technique is the resultant complexity inherent in the optomechanical and infrared detection technology used for the imaging system in order to achieve good speed, sensitivity and spatial resolution. Also, although direct detection of the infrared image can provide an acceptable qualitative visual representation of the temperature profile across the surface being viewed, the absolute accuracy of the measurement of temperature may be limited for a variety of reasons.

Another approach to observing and measuring the temperature across the surface is to first convert the temperature variations of the surface into thermally-encoded visible or near visible emissions before the radiation is detected and electronically processed. One such technique is to position a layer of luminescent material in thermal communication with the surface, such as by coating the luminescent material directly onto the surface. More conventional and less expensive imaging devices may then be used to detect and process the visible or near visible luminescent emissions. One such technique is to coat the surface with conventional thermographic phosphors and then detect the intensity of the luminescent image, much like any other optical image. This provides a good visual representation of temperature variations across the surface but suffers from a limited range of measurement and inaccuracies when quantitative measurements of temperature are desired. Thus, others have suggested variations of the luminescent material plus further optical processing of the luminescent image, such as by a pixel-by-pixel ratioing of the intensities of two separate and thermally dissimilar wavelength bands of luminescent emission. Given the right optics and luminescent material, this ratio is proportional to temperature. It has also been suggested to measure, on a pixel-by-pixel basis across the image, the decay time of the luminescence of a coating after the coating is excited by a pulse of excitation radiation. The decay time of the luminescent emission of selected materials is proportional to the temperature of the luminescent material over a given range of interest.

However, a totally satisfactory approach to such luminescent image decay time analysis does not yet exist. Therefore, it is a primary object of the present invention to provide this needed solution. An important goal of the present invention is a low-cost, simple, reliable and easy to use system that gives fast, accurate temperature measurements across a two dimensional luminescent surface over a wide range of temperatures.

Use of the luminescent decay time technique for measuring the temperature of a single small spot of luminescent material is becoming widespread. Optical fiber temperature measuring systems are commercially available. A very small quantity of luminescent material is formed as part of a sensor at the free end of an optical fiber, the other end of the optical fiber being connected to a measurement instrument. The instrument repetitively sends pulses of excitation radiation down the fiber and receives back from the sensor, in between the pulses, the decaying luminescent signal which is typically approximately exponential in time. A quantity proportional to the luminescent decay time, which is indicative of the temperature of the sensor, is then obtained by one of several signal processing techniques. One such technique is to measure the time it takes for the decaying intensity signal to fall from one value to another value that is the first value divided by e. This time is by definition the decay time of the luminescence. Another technique is to integrate the decaying luminescent signal over two different periods and then compare the integrated values, such as by ratioing them. Yet another technique is to digitize the decaying luminescent signal and subsequently analyze the digitized data to determine the decay time from the best fit of an exponential curve to the data samples.

Currently, a typical fiberoptic temperature measuring system includes only one or just a few optical fiber probes connected to a common optical instrument and signal processing system. It is another object of the present invention to provide such a instrument and system that can be used to multiplex hundreds or even thousands of separate optical fiber probes, and thus provide separate temperature measurements from each of the probes at a reduced cost per probe relative to what is now possible.

SUMMARY OF THE INVENTION

These and additional objects are accomplished by the present invention, wherein, briefly and generally, the luminescent radiation is imaged onto a two dimensional array of charge coupled devices (CCDs) of the type that is used as the "retina" in industrial and commercial solid state video cameras, and which is readily available through commercial supply channels. The way that a CCD camera array is operated has been recognized to be especially adapted for use in making measurements of the decay time of luminescent radiation that strikes it. Each photosite of the array integrates the amount of electronic charge that is generated by incident light during a single video frame. The luminescent material is chosen to have a range of decay times over a temperature range of interest that allows two intervals of a decaying signal to be integrated in successive video frames, either from a single decaying function or from two immediately sequential decaying functions. These two sets of integrals are then compared, by example, by ratioing or taking the difference over the sum, and this comparison is then converted to temperature by an empirically developed function or lookup table. An excitation source directs pulses of radiation against the luminescent material with a timing that is precisely coordinated with the frame rate of the CCD camera. A quantity proportional to the decay time of luminescent radiation striking each photosite is constructed in substantially real time every few video frames, the number of frames depending upon the particular signal processing technique that is chosen to be implemented.

Such a CCD array operated in this manner is used for non-contact surface temperature measurements by imaging onto the array emissions from a thin luminescent layer whose thermal pattern corresponds to that of the surface of interest, either by direct contact of the luminescent layer with the surface or by imaging the emissions from the surface onto a thin luminescent screen in a manner to produce a thermal image of the surface on the screen. The luminescent layer is excited to luminescence by repetitive pulses of excitation radiation, the CCD camera array then analyzing the transient characteristics of the resulting luminescence.

Such a CCD camera array can be similarly operated as a multiplexer with a large number of optical fiber luminescent sensor probes by optically coupling each individual probe through its optical fiber to one or more CCD photosites that do not receive a luminescent signal from any other probe. Since a typical CCD camera array includes well over 100,000 individual photosites, in order to provide a high level of resolution for two dimensional imaging, its adaptation as a common detecting and measuring instrument for a large number of optical fiber probes allows an equal number of such probes to be used with it. Of course, few temperature measuring installations would utilize that many individual independent optical fiber probes but it shows the very high capacity that is made available as compared with only a handful of such probes currently being used with a single fiberoptic thermometry instrument. Alternative to use of a two-dimensional array, a linear CCD array may be used for the multiplexing application. Linear CCD arrays are commercially available with from 100 to 1000 individual photosites. Even if only a small proportion of the total available capacity of either a two-dimensional or linear CCD array is utilized, the cost of the system on a per-sensor basis can be significantly reduced relative to current multi-sensor instrumentation systems.

Additional objects, features and advantages of the various aspects of the present invention will become apparent from the following description of its preferred embodiments, which description should be taken in conjunction with the accompanying drawings.

DESCRIPTION OF THE PREFERRED EMBODIMENTS

Figure 1:
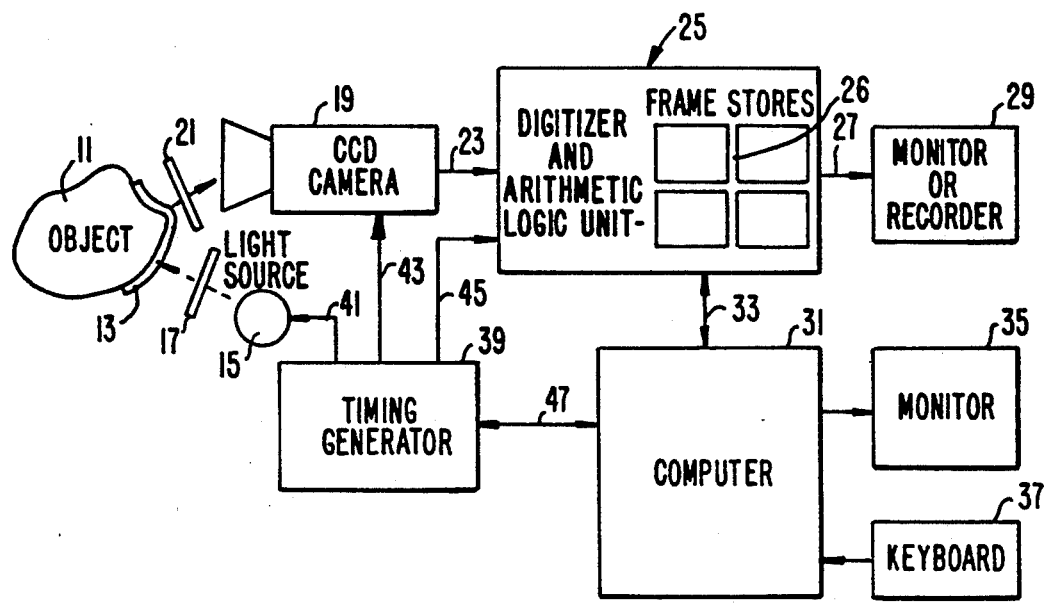
FIG. 1 is a block diagram of a remote, real time surface temperature measuring system that utilizes the present invention.

Referring initially to FIG. 1, a technique and system is generally described for accurately measuring the temperature profile across the surface of an object 11. The object 11, shown in FIG. 1 as a generalized one, is one which has an exposed surface to be monitored and which has a layer 13 of luminescent material placed in contact with the surface in order to result in good thermal transfer from the surface to the layer 13. This contact can be provided, for example, by painting the luminescent material directly onto the surface. Alternatively, the layer of luminescent material can be included as part of an elastic sheet that is placed onto the object surface. The types of objects represented by the general object 11 can include aircraft and aerospace models in a wind tunnel, operating electronic components or electronic assemblies such as printed circuit boards, portions of the human body, and the like.

An excitation light source 15 directs light against the layer 13 through an optional filter 17. The resulting luminescence from the layer 13, is viewed by a CCD camera 19 through an optional filter 21. Since luminescent materials, as is well known, emit radiation in a wavelength band that is different from the band in which it absorbs excitation radiation, the filters 17 and 21, if utilized, are provided for the purpose of isolating radiation of the excitation source 15 from the camera 19. That is, the filter 17 preferably has a bandpass within the luminescent material's absorption band so the wavelengths outside of that band do not reflect off the layer 13 into the camera 19. Similarly, the filter 21, if utilized, is selected to have a bandpass that includes the luminescence but excludes the excitation wavelengths that pass through the filter 17. Otherwise, the filter 21 can be a very broad band filter so that all the luminescent radiation from the layer 13 is received by the CCD camera 19.

An analog output of the CCD camera 19, in a circuit 23, is received by an electronic processing and control circuit 25. It is in this block 25 that the raw analog frames of data from the CCD array of the camera 19 are initially stored, manipulated and analyzed. A resulting temperature related signal is outputed in a circuit 27 to a real time monitor or to a data or video recorder 29. A system controlling computer 31 also receives, through circuits 33, the resulting temperature related signals. The computer 31 is used to control the system and may include a monitor 35 and a keyboard 37. A timing generator 39 is important to the system, coordinating operation of the excitation light source, over control circuit 41, the CCD camera 19, over control circuit 43, and the electronic processing and control circuits 25, over circuit 45. A circuit 47 between the computer 31 and the timing generator 29 allows an exchange of control and status information between these two portions of the system. In a more compact version of the system, the computer 31 may be replaced by a microprocessor chip mounted on the electronic processing and control circuit 25. In this situation, the computer monitor 35 would disappear and the keyboard 37 would be replaced by control switches and firmware.

Figure 2:
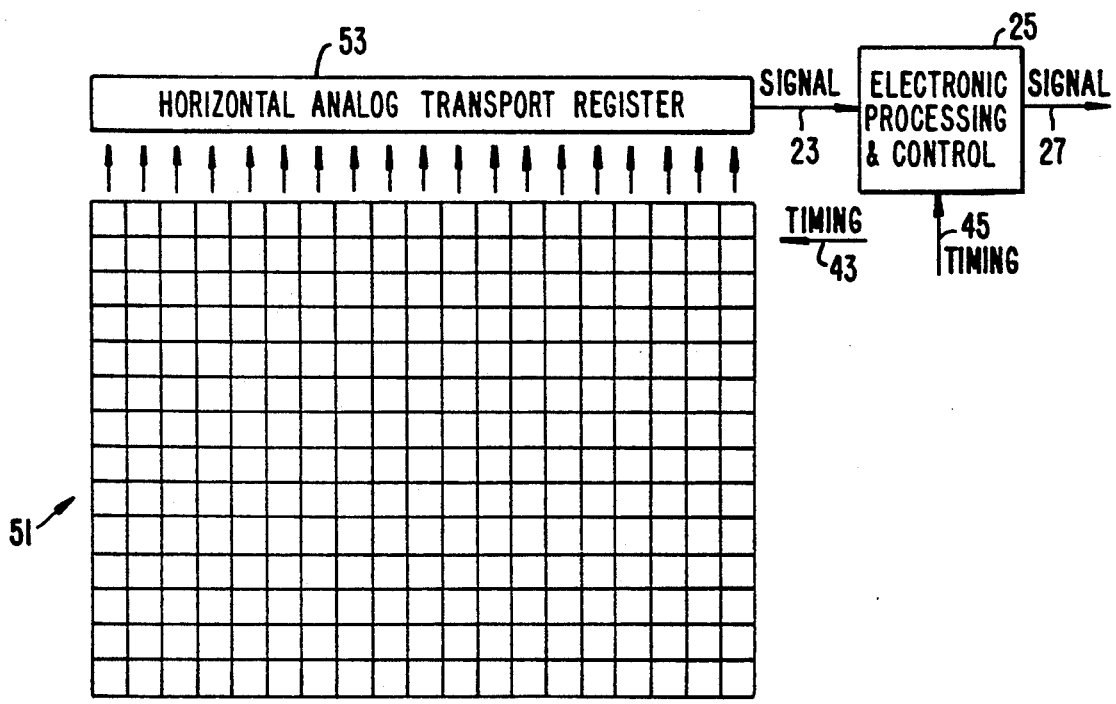
FIG. 2 schematically illustrates a CCD camera array of the type utilized in the system of FIG. 1.

Referring to FIG. 2, operation of a CCD camera array of the type utilized in the present invention will be very briefly described. Since such arrays are commercially available in substantial volumes, practically no physical modification of the commercially available arrays is required. The most significant adaptation to available CCD arrays in order make them useful in the applications being described is in a particular control of their operational frequency (frame rate) and timing, in a manner described below.

The CCD camera array illustrated in FIG. 2 is not intended to be complete or comprehensive but rather to provide a background for the subsequent discussion of its operation. A two-dimensional array 51 of individual photosites generally has them arranged in columns and rows. Only 19 columns and 14 rows are shown in FIG. 2 for simplicity. One standard CCD array, however, includes 430 columns and 488 rows, for a total of 209,840 individual photosites. The array is constructed as an integrated circuit on a single silicon substrate less than one inch on a side.

Each CCD photosite builds up an electronic charge in an amount proportional to the intensity of light striking it and the time over which the light is incident on it. Alongside each photosite is a vertical shift register. The electronic charge that is accumulated in each photosite during a frame of operation of the array is moved from the array to the electronic processing and control system 25 by first shifting these analog charge packets in the vertical shift registers, and thence through a horizontal shift register 53 and out of the array. Each frame of data consists of a sequence of signals corresponding to the individual photosite charge packets, the identity of each individual photosite signal being determined by its time of arrival with respect to some reference frame time. Each frame of data is stored in one of several frame stores 26 and then, at an appropriate time, retrieved and processed in the manner described below.

As can be seen, a great deal of data is processed as a result of one frame of operation of the CCD camera array since it will have over 100,000 individual photosites and thus that many individual pieces of data. A typical CCD camera frame rate is 60 frames per second, meaning that all this happens in about 17 milliseconds. The frame rate of available CCD camera arrays can be adjusted significantly, however, if necessary to match to the decay time characteristics of the luminescent material chosen or to otherwise facilitate the large amount of signal processing that needs to occur in order for the system to operate in substantially real time.

Figure 3:
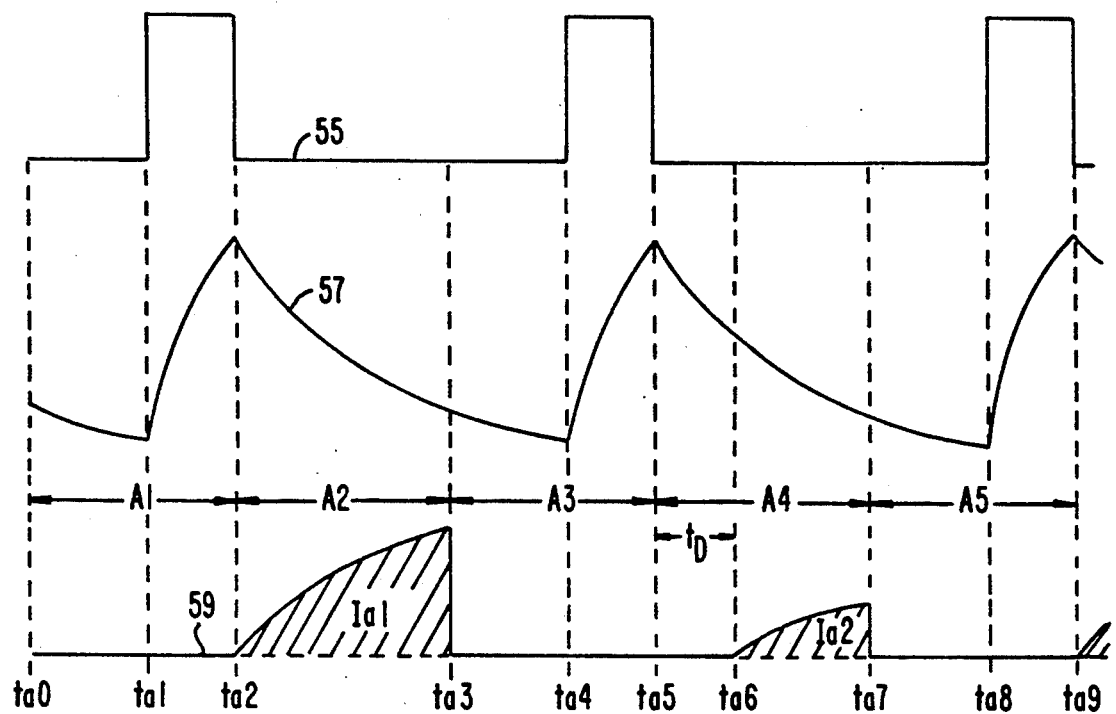
FIGS. 3-7 each illustrate a different specific way of operating the CCD camera array in the system of FIG. 1.

Referring to FIG. 3, one of five specific ways of operating the CCD camera of FIGS. 1 and 2 is described. A first waveform 55 represents the light pulses produced by the source 15 (FIG. 1) in response to commands from the timing generator 39 over the circuit 41. The light source 15 may be a flash lamp, light emitting diode (LED), solid state laser, or the like. A resulting luminescent signal from one small area of the layer 13 is shown by a curve 57. Each area of the luminescent layer 13 produces an emission pulse with a unique shape of its time dependence that is dependent upon its temperature. As can be seen from FIG. 3, the luminescence signal 57 builds up during the excitation pulse, and then decays in a substantially exponential manner until a subsequent excitation pulse, at which time the process begins again.

In the example of FIG. 3, the CCD camera 19 is illustrated to have successive frames A1, A2, A3, A4, A5, and so on, each having the same duration. The timing generator 39 is configured to emit an excitation pulse that ends coincidentally with the end of every other frame. This occurs at time ta2, at the end of frame A1, and at time ta5, at the end of the frame A3.

A signal 59 of FIG. 3 shows the output of a single photosite of the CCD camera array. In this embodiment, any output data during the frames in which the excitation pulse occurs is sacrificed. Thus, the photosite output signal 59 is shown to be zero during frames A1, A3 and A5. However, in an actual operation, the photosite output signal will likely have some value during each of those frames but the signal is not retained by the frame stores 26 of the signal processing circuitry during those frames. Therefore, it is shown in FIG. 3 to be zero since its value is of no interest.

In order to measure the temperature of the small area of the luminescent layer 13 (FIG. 1) that is imaged onto the photosite whose signals are being shown in FIG. 3, data from two successive periods of decay of the luminescent signal 57 (FIG. 3) are utilized. As noted by the signal 59, the timing generator 39 (FIG. 1) allows charge to be accumulated by the photosite throughout the entire duration of the frame A2, resulting in accumulation of a charge proportional to the area Ia1 under the curve. This is a time integral of that curve over the duration shown. During the next frame A4 of the next decaying signal cycle, charge is not accumulated for the normal frame period but rather this frame is begun at a delayed time $t_D$ after the beginning of the frame at time ta5. Thus, the integration period during this cycle is from time ta6 until time ta7 at the end of the A4 frame.

The resulting integration quantity Ia2 is then compared with the previous integration value Ia1 by ratioing them, by subtracting one from the other, by dividing the difference of the two by the sum of both of them, or by some other appropriate mathematical comparison. The result of this comparison is then converted to temperature by use of either a formula or a digital lookup table within the electronic processing and control circuits 25. Such a formula or table is empirically determined for the particular luminescent material being utilized. That is, a number of such measurements are made over the full range of temperatures likely to be to be encountered while selected temperatures are also measured by a thermocouple or other accurate reference sensor in order to acquire the formula or table which is used in this manner.

Figure 4:
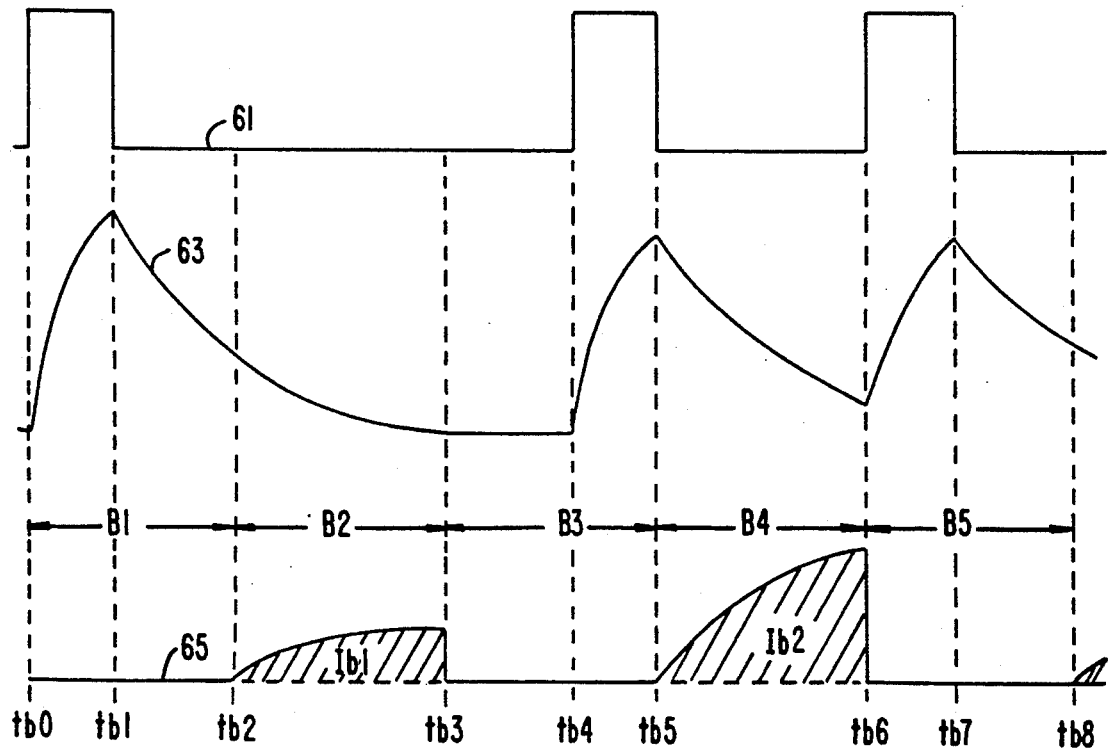

FIG. 4 shows a slightly modified version of the system operation of FIG. 3. A curve 61 shows repetitive excitation pulses which, in this case, are not periodically occurring as they are in the example of FIG. 3. Rather, one pulse is caused to appear during a first portion of one frame B1 while the next pulse occurs at the end of the frame B3. The next pulse reverts to occurring during the beginning of the frame B5, and so forth. This results in shifting a luminescent signal 63 in time with respect to the measurement frames B2 and B4. Charge is accumulated during these entire frames but a different portion of the decaying luminescent intensity signal 63 is integrated during those periods because of this shift of the relative timings of the excitation pulses. One complete cycle of operation is shown by the four frames B1 through B4. A comparison of the integrated values Ib1 and Ib2 allow the temperature to be measured of the luminescent layer area that is imaged onto the photosite.

Figure 5:
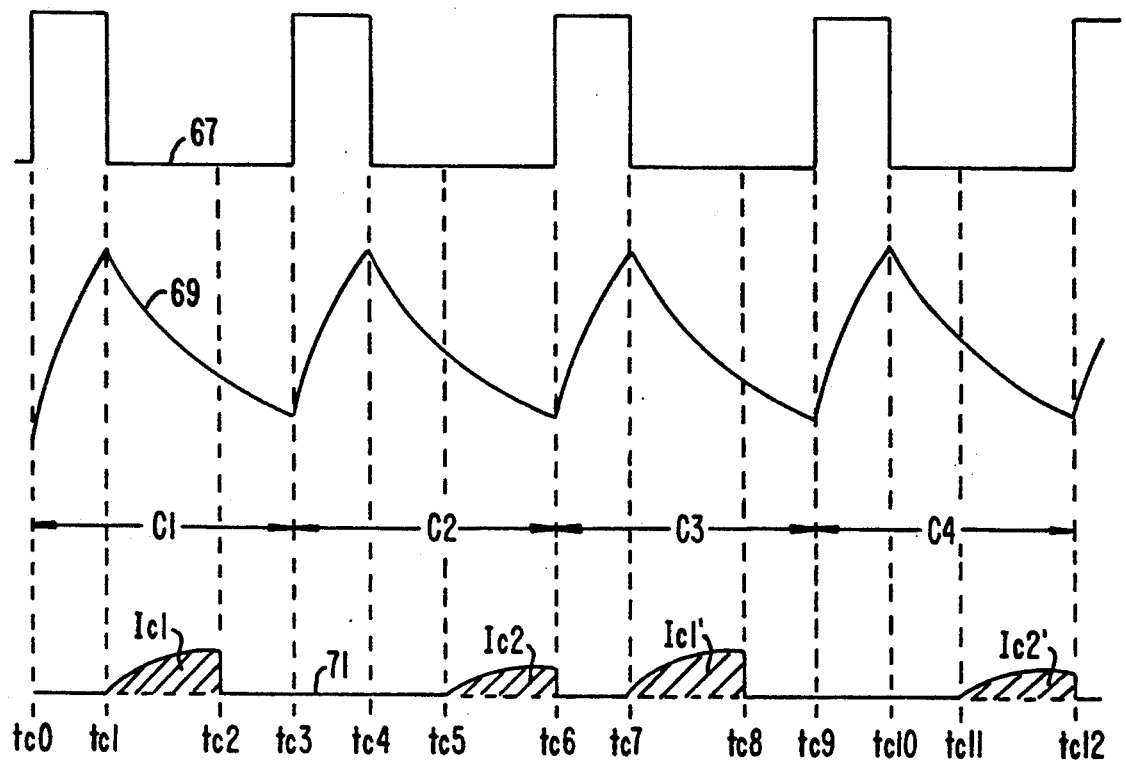

With reference to FIG. 5, a third specific signal processing alternative is illustrated. In this example, one excitation pulse is emitted at the beginning at each of the frames C1, C2, C3 and C4, as shown by a curve 67. The duration of each of the pulses is made to be a small part of each frame in order to have enough time remaining to analyze a decaying portion of a luminescent 69 during each frame. The period of charge accumulation of the photosite during each frame alternates between them. During a first frame C1, the signal 69 is acquired for a period beginning at time tc1 immediately upon termination of the excitation pulse. An integrated signal Ic1 is acquired from that time until a time tc2 which occurs before the end of the frame C1. In the next frame C2, a different portion of the decaying luminescent curve is acquired, from a time tc5 until the end of the frame C2 at the time tc6. It is the integrated signal Ic2 acquired during the frame C2 that is compared with the integrated charge value Ic1 acquired during the immediately preceding frame C1.

Thus, it can be seen from FIG. 5 that a temperature measurement is made in only two successive frames of the CCD camera array while four such frames are required for a single measurement in either of the implementations shown in FIGS. 3 or 4. Of course, this requires either using a luminescent material with a shorter decay time characteristic in the implementation of FIG. 5, or a longer video frame duration, or both, than with the implementations of FIGS. 3 and 4. As is apparent from reviewing the operation waveforms being described, it is important that the luminescent material be chosen to have a range of decay times over the range of temperatures to be encountered that is properly matched with the CCD camera frame duration in order that enough luminescent signal exist during two different integration periods.

Figure 6:
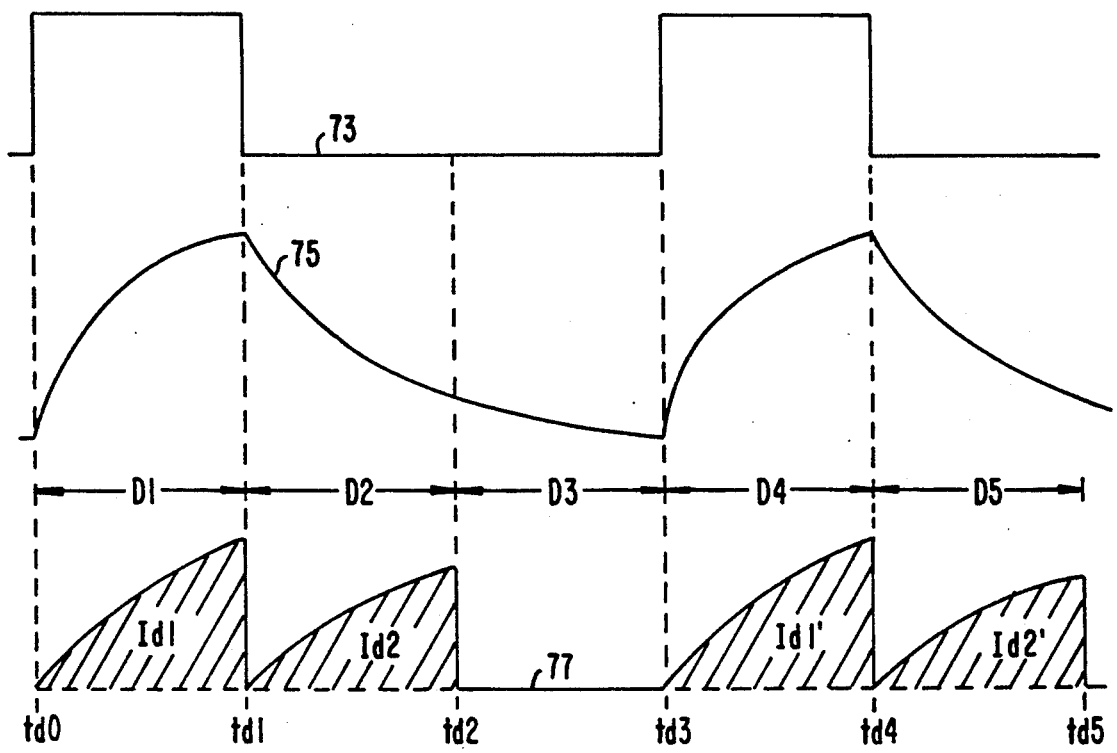

Referring to FIG. 6, yet another operational technique is illustrated. As shown by a curve 73 of the excitation pulses, one pulse is timed to occur every third CCD camera array frame. A complete operational cycle occurs during three successive frames, as shown during frames D1, D2 and D3. A resulting luminescent signal 75 is integrated simultaneously with the occurrence of the excitation pulse during the frame D1, thus acquiring an integrated quantity Id1 of an output signal 77 of a single photosite. The second integration Id2 occurs during an initial portion of the luminescent decay that occurs during the frame D2. No signals acquired during the frame D3 in order to allow the luminescent signal 75 more time to decay to an appropriate beginning intensity. A comparison of the two integrations Id1 and Id2 thus gives the temperature. In this technique, the filters 17 and 21 must almost certainly be used to prevent the CCD camera from being blinded by the excitation pulses.

Figure 7:
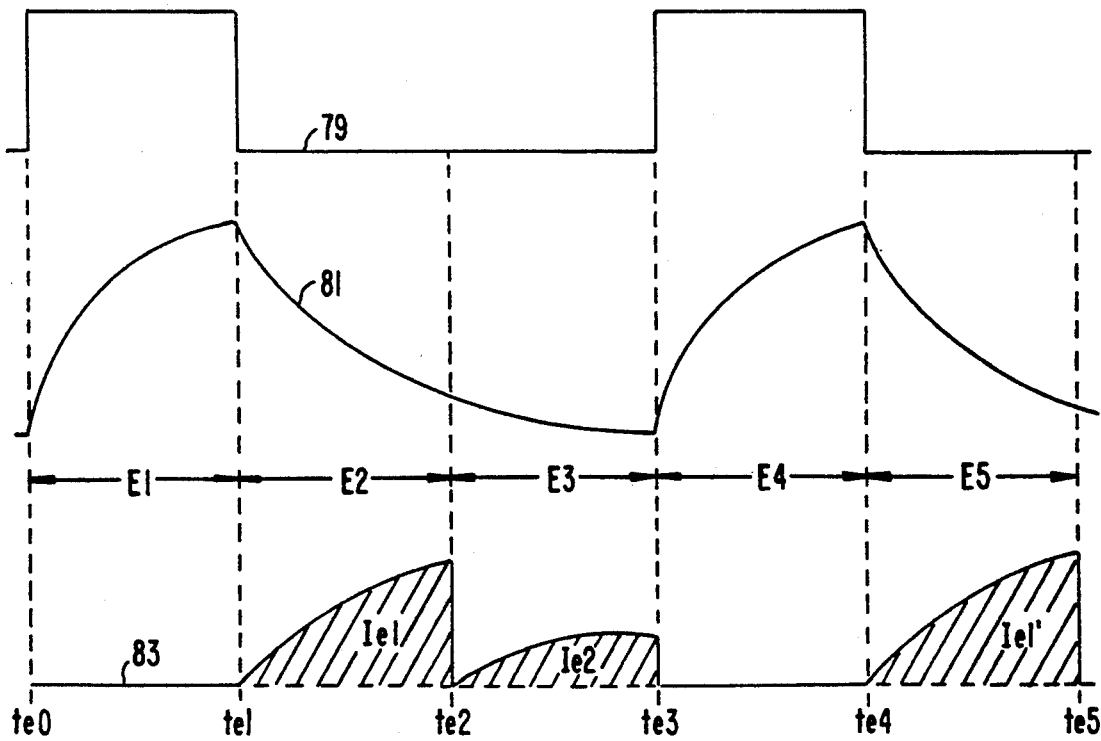

A final example of the CCD camera array operation is given in FIG. 7. The excitation radiation pulses shown in a curve 79 are the same as those in the curve 73 of the FIG. 6 embodiment. Similarly, a signal 81 of the luminescent emission striking the one photosite being evaluated is the same as the curve 75 of FIG. 6, assuming that the luminescent materials and other conditions are all the same. What is different, as shown by a curve 83, is that the output of the photosite represented by that curve is utilized during the final two of a three frame cycle, rather than the first two frames as shown in FIG. 6. A first part of the decaying signal is integrated during the entire frame E2, resulting in an integrated quantity Ie1 that is compared with a quantity Ie2 that is the integration of the luminescent signal in the next successive frame E3. A ratio of these two integrated quantities or some other appropriate comparison thus leads to temperature.

The operational technique illustrated in FIG. 7 is generally preferred, primarily for the reason that both of the photosite quantities which are compared in order to make a single temperature measurement are acquired from a single luminescent decay curve. It will be noted from the examples of FIGS. 3, 4 and 5 that one of the two quantities to be compared is obtained from a different luminescent decay function. That is, each of the two photosite integration quantities are obtained as a result of a different excitation pulse. It is preferable to acquire both quantities as a result of a single excitation pulse, as in the preferred embodiment of FIG. 7, in order to eliminate any variations that may occur from excitation pulse to excitation pulse. Any such variations cause non-temperature variations in the resulting luminescent signal. This disadvantage of the embodiments of FIGS. 3, 4 and 5 can be minimized by averaging a number of measurements but the necessity of doing this requires more time to determine a temperature value. In applications where the temperature may be varying and such a variation is desired to be monitored in substantial real time, this can be a disadvantage. The embodiment of FIG. 6 has the same advantage as that of FIG. 7 but is not preferred since one of the photosite integrations occurs during the excitation pulse, thus being susceptible to the photosite receiving excitation radiation in cases where the filters 17 and 21 do not adequately suppress the amount of excitation light reaching the CCD camera.

As previously mentioned, any operable system will have the decay time characteristics of its luminescent material matched to the frame rate of the CCD camera that is being used. The decay time of the luminescent material appropriate for the FIG. 5 embodiment must be the shortest, or the video frame would rate the longest, of the five embodiments being described. Conversely, the embodiments of FIGS. 6 and 7 require the longest decay rate in a luminescent material, or the shortest frame rate, among the five embodiments being described.

Although there are a wide variety of luminescent materials with decay times long enough to be useable in these embodiments, one has been found that appears to be particularly suitable. This material is chromium-activated yttrium orthoaluminate ($YALO_3:Cr$) in powder form. This material can be excited in the visible range of the electromagnetic energy spectrum, with green or blue-violet light. The luminescent emissions are well separated from the excitation radiation, being within the deep red and near infrared. The material has a fluorescent decay time which varies nearly linearly with temperature from 54 milliseconds at $-200°$ C. to about 10 milliseconds at $+300°$ C. At $+425°$ C., this material has a decay time of about 4 milliseconds. This range of decay times is suitable for use with a standard video frame rate of 60 Hz, resulting duration of each frame being about 17 milliseconds. In addition to these favorable characteristics, the material is thermally stable, melting above $1800°$ C., and has other characteristics that are required for a luminescent material to be useful in any temperature measuring application.

The principal disadvantage of all these schemes is that several input frames are required in order to output a single frame of processed data. This may be compensated in part by running the CCD camera at higher than normal frame rates. A limit will probably be set, however, by the resolution of the thermal data being processed. Alternatively, data rates can be increased by ganging together adjacent photosites, but this obviously decreases spatial resolution. Another alternative is to obtain the data in real time, store all the raw data and then, if it is desired to retain both full spatial and thermal resolution, do the processing later at whatever speed is required, followed by representing the data either in real time or slow motion. Clearly, the specific application will determine the best approach.

The use of data acquired from two fresh frames has been described in each of the embodiments of FIGS. 3–7 in order to make a single temperature measurement. That is, the data of each frame is used only once. The speed of the process can be increased, however, if some of the frame charge integrals are used in more than one calculation of temperature. There are two specific ways to do this. One is a "rolling" processing technique wherein each charge integral is compared with the immediately preceding charge integral. Thus, each is used in two successive comparisons and temperature calculations. The result is twice the number of temperature measurements in the same amount of time.

The second way of using a frame measurement more than once is to hold one frame measurement as a reference and then compare each of successively acquired frame data with that reference for a number of frames, until finally the reference frame is freshly measured. For example, with reference to FIG. 3, the charge integral Ia1 could be used as a reference and the shortened period charge integral Ia2 then measured in each of several successive frames after that, a temperature calculation being made after each of these successive frames as a result of comparing the shortened time charge integral with the reference full frame charge integral Ia1. Four frame stores 26 provide enough storage capacity to implement this variation. A disadvantage of this technique is that rapidly changing temperature is not followed as rapidly as it is with the methods earlier described, since one quantity being compared as part of each temperature measurement remains unchanged for several successive frames.

Another way of speeding up the rate at which temperature measurements are made is to use two or more CCD cameras that are operated in staggered sequence. The same image field is focused onto each of multiple CCD cameras. Even though the operational rate of each camera is not increased, the rate of temperature measurements is increased by the overall system.

Each of the operational embodiments of FIGS. 3–7 have assumed that the video frame rate is fixed over the full range of temperatures which can be measured. However, in order to take full advantage of luminescent materials that have a widely varying decay time over a temperature range of interest, it may be desirable, when such materials are utilized, to vary the CCD camera array frame rate as a function of temperature. The reason for doing so is to maximize the amount of signal that is detected during the frames where integration occurs. For example, as the decay time becomes very short with extremely high temperatures, it would be desirable to shorten the duration of each frame (increasing the frame rate) in order to better match the signal processing to the decay time being experienced at the moment. Another approach is to provide manually or automatically selectable two or more ranges of operation wherein the frame rates are set to be different when measurements are being made in each of two or more temperature ranges.

It is desirable to compensate, as part of the data processing, for any differences in the characteristics of the individual CCD photosites. Their individual dark currents are determined by imaging a dark field onto the entire array and storing the integrated charge measured in one frame. This then becomes data that is permanently stored in the system. The stored dark current value for each photosite is subtracted from each measured charge integral in order to compensate for it. Similarly, the CCD camera is exposed to a light field of uniform brightness, any variations in integrated charge readings during one test frame being used as a multiple of subsequent readings in order to provide additional compensation for sensitivity variations from photosite to photosite.

Figure 8:
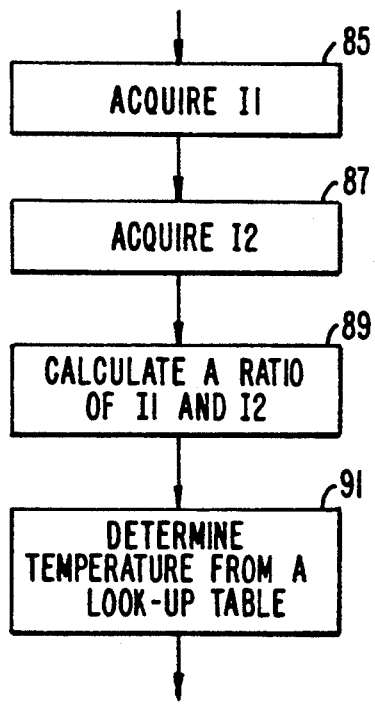
FIG. 8 is a flow diagram illustrating the processing of the signals obtained from the CCD camera array in the system of FIG. 1 when operated in accordance with any of the ways illustrated in FIGS. 3-7.

Referring to FIG. 8, a brief flow chart illustrates the nature of the calculations done by the processing and control system 25 (FIG. 1), according to one method, for any of these specific embodiments of FIGS. 3–7. The processing begins, in steps 85 and 87, by acquiring the frames of integrated charges I1 and I2 in accordance with any of the five embodiments of FIGS. 3–7. These two sets of values are then digitized and, in a step 89, the values are compared, preferably by taking a ratio, but other comparison techniques as mentioned previously can be utilized. This ratio is then used in a step 91 to calculate or look up the temperature using an empirically determined formulation or look-up table, as previously discussed. The resulting temperature of each small area of the object surface is used to form a display or is recorded.

Several alternative ways have been described for determining temperature of a single point of the luminescent material 13 that is imaged onto the single CCD camera photosite. The same process occurs for each of the other photosites, depending on the size of the CCD camera array that is utilized. The temperature calculation for each such image point can then be utilized in a number of different ways. The raw data, in computer form, can be analyzed, the temperature values then converted to values of color and displayed on a color monitor, or recorded by a color printer, to show surface temperature variations as variations in pseudo-color. These temperature values can also be used for industrial control, some action occurring in response to the occurrence of a certain temperature pattern. The applications are numerous when precise temperature data are made available. By using commercially available CCD camera arrays, the data is obtained in a form that can easily be utilized by either standard computer or video imaging equipment.

Figure 9:
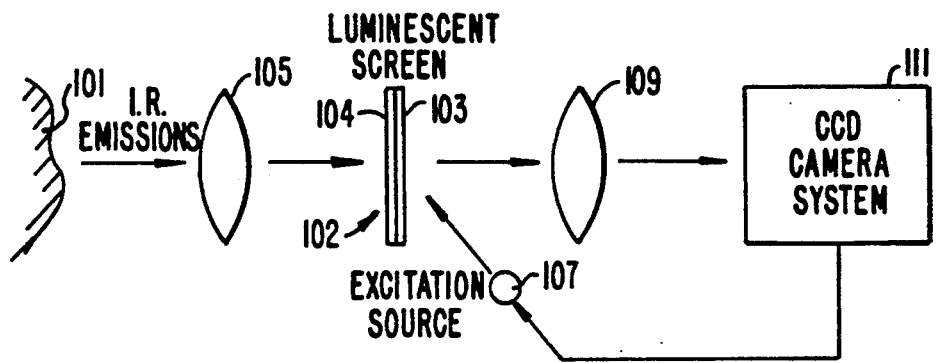
FIG. 9 shows a modification of the system of FIGS. 1-8 wherein the luminescent screen is separated from the object surface being measured and imaged.

Referring to FIG. 9, an alternative implementation is described. An object surface 101 is desired to be monitored and its temperature measured. Rather than coating the luminescent material directly on the object surface, however, as was done in the embodiment of FIG. 1, a thin layer 103 of luminescent material is included as part of a screen 102 that is physically removed from the object surface 101. The screen 102 includes an infrared absorbing material layer 104, such as a blackened layer of an appropriate material. The infrared emissions from the object surface 101 are then imaged by an appropriate optical system 105 onto the layer 104. The layers 103 and 104 of the screen 102 are held in intimate contact with each other in order to provide for good thermal transfer from the infrared image absorbing layer 10 to the luminescent layer 103. The luminescent layer is thus heated in accordance with the infrared image from the object surface. The thermal mass of the screen 102 is made to be as low as possible in order to allow it to rapidly respond to changes in the infrared image on the layer 104.

The luminescent layer 103 is caused to luminesce by an excitation source 107. The visible or near visible luminescent emissions from the layer 103 are imaged by an appropriate optical system 109 onto a CCD camera system 111. A pair of optical filters may optionally be employed, similar to the system of FIG. 1. The CCD camera system 111 is of the type previously described with respect to FIGS. 1–8. Operation of the system of FIG. 9 is also the same except that the screen 102 serves to convert the heat image of the surface 101, instead of placing the luminescent material in direct contact with the surface of interest.

An advantage of the system of FIG. 9 is that a true infrared camera results. All of the elements shown in FIG. 9 (except, of course, the object's surface 101) are packaged together as a single instrument. This instrument can be of very small size and low cost when compared to existing infrared cameras. The system can operate at room temperature and no mechanical scanning is required. However, calibration of the system does still require a method of relating temperature variations in the image plane (screen 102) to the temperature variations of the surface 101, a problem common to all infrared cameras (thermographs).

Figure 10:
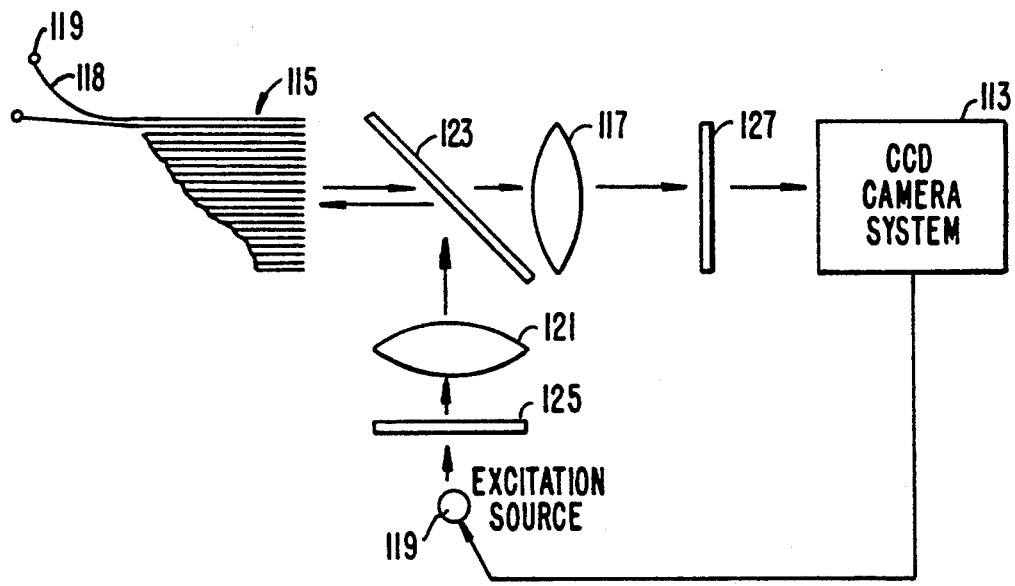
FIG. 10 shows another modification of the system of FIGS. 1-8 wherein a large number of optical fiber ends are bundled together and imaged onto the CCD camera array in place of the two dimensional luminescent surface, each optical fiber having a temperature sensor at its end.

Referring to FIG. 10, a different use of a similar type of CCD camera system 113 is explained. Rather than luminescence from a two dimensional surface being imaged onto the CCD camera array, a large number of optical fibers are formed into a bundle 115 so that their ends terminate in a common plane which is then imaged by an appropriate optical system 117 into the CCD camera 113. Each of the optical fibers within the bundle 115 can carry a separate, independent luminescent optical signal whose decay time is to be measured. In a preferred embodiment, each of the optical fibers terminates in a temperature sensing probe, such as a fiber 118 having a temperature sensing probe 119 formed at its end. The temperature sensing probe 119 contains luminescent material, as currently commercially utilized and discussed in the literature. In this use, a number of independent sensors can be utilized that are equal to the number of photosites within the CCD array of the camera system 113. A tight bundle of the optical fiber ends is then imaged onto that array by the optics 117 in a manner that each optical fiber end is imaged onto a unique one or more of the CCD photosites. As an alternative to the CCD camera with a two-dimensional array of photosites, a linear array may be used for this application. In either case, the system is as much a multiplexer as an imager, the image simply being used to identify each sensor by its location in the image.

In order excite all of the luminescent sensors at the end of the large number of optical fibers, an excitation source 119 periodically generates pulses which are focused by an optical system 121 onto the exposed ends of the fibers within the bundle 115. A dichroic beam splitter 123 is utilized to reflect the excitation light onto the fibers while at the same time allowing the different wavelength band of the luminescence to pass through it and onto the CCD camera system. Optical filters 125 and 127, having nonoverlapping wavelength bandpass characteristics, are optionally employed in order to eliminate, to the extent possible, radiation of the excitation source 119 from reaching the CCD camera 113. When employed, the filter 125 passes a wavelength band of electromagnetic radiation to excite the luminescent material of the sensors, excluding all else, and the filter 127 passes another band of wavelengths corresponding to that of the luminescence from the sensors, excluding all else.

As mentioned previously, the advantage of this approach is that a very large number of optical fiber luminescent probes can be utilized with a single CCD camera array based instrument. The complexity and cost of a multi-sensor temperature measuring system is thus reduced significantly.

Although the invention has been described with respect to its preferred embodiments, it will be understood that the invention is to be protected within the full scope of the appended claims. For example, even though the preferred embodiments deal with only temperature measurement, it will be understood that the measuring system of this invention is equally useful for the measurement of other parameters. The only requirement is that the parameter being measured somehow affects the rate of luminescent decay in a measurable way. The system of the present invention then provides an improved way of measuring that rate of decay. The novel use of the CCD camera array according to the present invention has application anywhere there is a decaying optical signal whose properties are desired to be utilized for either visualization or measurement. The signal could, for example, be from a fluorescent gas layer and the data obtained could be used to acquire flow information rather than temperature alone.

It is claimed:

1. A method of measuring a condition of an object or environment, comprising the steps of:

positioning in communication with said object or environment a quantity of luminescent material that is characterized by emitting, in response to a pulse of excitation radiation, luminescent radiation having a rate of decay that is related to a level of said condition, directing repetitive pulses of excitation radiation against the luminescent material, thereby to cause a resulting luminescent radiation to follow a repetitive cycle of building up during the excitation pulses and thence decaying between pulses at a rate related to the level of said condition, positioning in the path of said luminescent radiation at least one radiation detector characterized by generating an electrical charge that is related to a level of said radiation and accumulates the charge for gated periods of time, gating said at least one detector in synchronism with the excitation radiation pulses and in a manner to obtain values corresponding to the charge accumulated during two different intervals relative to the luminescent material emission cycle, comparing the accumulated charge values during said two different intervals, and converting the charge value comparison to a magnitude of said condition.

2. The method of claim 1 wherein the accumulated charge obtained during two different intervals relative to the luminescent material emission cycle as part of the gating step includes timing said intervals to occur during the same luminescent cycle.

3. The method of claim 2 wherein timing of said intervals is further caused to occur during the decaying of the luminescent radiation between excitation pulses.

4. The method of claim 1 wherein the intervals of the gating step do not overlap each other with respect to the luminescent radiation cycle.

5. The method of claim 1 wherein the repetitive pulse directing step includes directing the repetitive pulses at periodic intervals.

6. The method of claim 1 wherein the charge comparing step includes taking a ratio of the accumulated charge values.

7. The method of measuring a condition of a plurality of areas of a luminescent material that is characterized by emitting, in response to a pulse of excitation radiation, luminescent radiation having a rate of decay that is related to a level of said condition, comprising the steps of:

directing repetitive pulses of excitation radiation against the luminescent material, thereby to cause the luminescent radiation to follow a repetitive cycle of building up during the excitation pulses and thence decaying between pulses at a rate related to said condition, positioning in a path of said luminescent radiation an array of charge coupled device elements, imaging said luminescent radiation onto said element array with said luminescent material areas matched to individual elements of said charge coupled device array, gating said charge coupled device array elements in synchronism with each other and with the excitation radiation pulses to operate during two different intervals relative to the luminescent material emission cycle, comparing an output during said two different intervals for the individual charge coupled device array elements, and converting the compared outputs to said condition, whereby the condition comparisons from each of the charge coupled device array elements corresponds to an area of the luminescent material.

8. The method of claim 7 wherein the condition being measured is temperature and the individual areas of luminescent material are adjacent each other across a layer of luminescent material that is physically attached to a surface of an object, whereby the temperature is being measured across the surface of the object.

9. The method of claim 7 wherein the condition being measured is temperature and the individual areas of luminescent material are adjacent each other in a layer of said luminescent material extending across a screen that also has an infrared absorbing layer in thermal contact with the luminescent layer, said method comprising the additional step of imaging an infrared image of an object surface onto said infrared absorbing layer, whereby the temperature of the object surface is being measured thereacross.

10. The method of claim 7 wherein the condition being measured is temperature and said plurality of areas of luminescent material are distributed in a plurality of temperature sensors carried by lengths of optical fibers, and wherein the imaging step includes imaging luminescence from free ends of the optical fibers onto said element array, whereby the temperatures of the plurality of sensors are measured.

11. The method of claim 7 wherein the luminescent radiation imaging step includes imaging said luminescent material areas onto said element array through a bundle of optical fibers by matching individual of said optical fibers with individual elements of said array of charge coupled device elements.

12. The method of claim 7 wherein the gating step includes timing said two different intervals to occur during the same luminescent material emission cycle.

13. The method of claim 12 wherein timing of said two different intervals are further caused to occur during the decaying of the luminescent radiation between excitation pulses.

14. The method of claim 7 wherein the intervals of the gating step do not overlap each other with respect to the luminescent radiation cycle.

15. The method of claim 7 wherein the repetitive pulse directing step includes directing the repetitive pulses at periodic intervals.

16. The method of claim 7 wherein the output comparing step includes taking a ratio of the output during said two different intervals.

17. A method of obtaining a visual image of a temperature profile across an area of a surface, comprising:

coating said surface with a layer of luminescent material that is characterized by emitting, in response to a pulse of excitation radiation, luminescent radiation having a temperature related rate of decay, directing repetitive pulses of excitation radiation against the luminescent material layer, thereby to cause the luminescent material radiation emission to follow a repetitive cycle of building up during the excitation pulses and thence decaying between pulses an amount related to temperature, imaging said luminescent emission onto a two dimensional array of charge coupled device elements characterized by generating individual element signals representative of an accumulation of luminescent emission radiation intensity falling thereon over a period of time, thereby to detect said luminescent material emission from adjacent points of said surface area, gating said charge coupled device elements relative to timing of the excitation radiation pulses and during two different intervals of the luminescent radiation emission cycle, thereby to generate two individual charge coupled device element signals for a luminescent radiation cycle, comparing said two signals individually from the charge coupled device elements, converting the individual charge coupled device element signal comparison into temperature, and generating from the individual element temperature conversion a visual image corresponding to temperature across said surface area.

18. An imaging device, comprising:

a video camera including a two-dimensional array of charge coupled device elements that are individually characterized by generating, after repetitively occurring frames, a signal that is related to an integrated value of electromagnetic radiation striking the element during the preceding frame, means including a timing circuit for controlling the timing of said camera frames, a source of excitation radiation for a luminescent material, means synchronized with said camera frame controlling means for causing said radiation source to emit a sequence of pulses with time durations therebetween, and means receiving the individual element signal outputs for comparing successively occurring pairs of such signals therefrom.

19. An infra-red camera, comprising:

a video camera including a two-dimensional array of charge coupled device elements that are individually characterized by generating, after repetitively occurring frames, a signal that is related to an integrated value of electromagnetic radiation striking the element during the preceding frame, means including a timing circuit for controlling the timing of said camera frames, a screen having an infra-red absorbing layer on one side thereof and luminescent material on another side thereof, said luminescent material being characterized by emitting, in response to a pulse of excitation radiation, electromagnetic radiation having a rate of decay that is related to the temperature of the luminescent material, means for imaging an object onto said screen's infra-red absorbing layer, thereby to heat the screen in accordance with an infra-red emission image of the object, a source of excitation radiation directed at said screen's luminescent material layer, thereby causing an electromagnetic radiation emission therefrom with decay times that vary across the screen in accordance with the screen's temperature, means for imaging said luminescent material layer emission onto the charge coupled device element array, means synchronized with said camera frame controlling means for causing said radiation source to emit a sequence of pulses with time durations therebetween, and means receiving the individual element signal outputs for comparing successively occurring pairs of such signals therefrom.

20. A multi-channel condition measuring system, comprising:

a plurality of optical fibers having individual sensors at one end thereof, the individual sensors including a quantity of luminescent material that is characterized by emitting, in response to a pulse of excitation radiation, luminescent radiation having a rate of decay that is related to said condition, an array of charge coupled device elements that are individually characterized by generating, after repetitively occurring frames, a signal that is related to an integrated value of electromagnetic radiation striking the element during the preceding frame, a source of excitation radiation for said luminescent material, optical means positioned at ends of said optical fibers opposite said sensors for coupling said excitation radiation thereinto and directing the luminescence from their individual sensors onto individual ones of said charge coupled device elements, means including a timing circuit for controlling the timing of said camera frames, means synchronized with said camera frame controlling means for causing said radiation source to emit a sequence of pulses with time durations therebetween, thereby to cause the luminescent material radiation emission to follow a repetitive cycle of building up during the excitation pulses and thence decaying between pulses in an amount related to a level of said condition, and means receiving the individual element signal outputs for comparing successively occurring pairs of such signals therefrom.

21. The system according to claim 20 wherein said array includes a two-dimensional array of said elements.

22. The system according to claim 20 wherein said array consists of a linear array of said elements.

* * * * *